United States Patent
Kubo et al.

(10) Patent No.: US 10,595,764 B2
(45) Date of Patent: Mar. 24, 2020

(54) EMOTION IDENTIFICATION DEVICE, EMOTION IDENTIFICATION METHOD, AND EMOTION IDENTIFICATION PROGRAM

(71) Applicant: Japan Science and Technology Agency, Saitama (JP)

(72) Inventors: Kenta Kubo, Hiroshima (JP); Nobuyuki Kawai, Aichi (JP); Kazuo Okanoya, Tokyo (JP)

(73) Assignee: Japan Science and Technology Agency, Saitama (JP)

( * ) Notice: Subject to any disclaimer, the term of this patent is extended or adjusted under 35 U.S.C. 154(b) by 214 days.

(21) Appl. No.: 14/419,957

(22) PCT Filed: Mar. 18, 2013

(86) PCT No.: PCT/JP2013/057623
§ 371 (c)(1),
(2) Date: Feb. 6, 2015

(87) PCT Pub. No.: WO2014/024511
PCT Pub. Date: Feb. 13, 2014

(65) Prior Publication Data
US 2015/0196244 A1 Jul. 16, 2015

(30) Foreign Application Priority Data
Aug. 7, 2012 (JP) ................... 2012-174946

(51) Int. Cl.
*A61B 5/16* (2006.01)
*A61B 5/00* (2006.01)
(Continued)

(52) U.S. Cl.
CPC .............. *A61B 5/165* (2013.01); *A61B 5/024* (2013.01); *A61B 5/0205* (2013.01);
(Continued)

(58) Field of Classification Search
CPC .............. G09B 5/00; G09B 19/00; A61B 5/00
See application file for complete search history.

(56) References Cited

U.S. PATENT DOCUMENTS

| 5,450,855 A * | 9/1995 | Rosenfeld | A61B 5/0482 600/545 |
| 8,473,044 B2 * | 6/2013 | Lee | A61B 5/0476 600/544 |

(Continued)

FOREIGN PATENT DOCUMENTS

WO 2010001512 A1 1/2010

OTHER PUBLICATIONS

Kubo, K., Okanoya, K., & Kawai, N. (2011). Apology suppresses physiological but not psychological anger. 28th Annual Conference of the Japanese Cognitive Science Society (pp. 32-35).*
(Continued)

*Primary Examiner* — Jerry-Daryl Fletcher
*Assistant Examiner* — Daniel E Lane
(74) *Attorney, Agent, or Firm* — Amster, Rothstein & Ebenstein LLP

(57) ABSTRACT

An emotion identification device includes: a first detection unit which detects a central nervous system reaction of a user; a second detection unit which detects an autonomic nervous system reaction of the user; and an identification unit which identifies aggressiveness in anger of the user based on the central nervous system reaction and the autonomic nervous system reaction.

3 Claims, 2 Drawing Sheets

(51) Int. Cl.
    *G06Q 10/10*     (2012.01)
    *A61B 5/0205*     (2006.01)
    *A61B 5/024*     (2006.01)
    *A61B 5/0476*     (2006.01)

(52) U.S. Cl.
    CPC .......... *A61B 5/0476* (2013.01); *A61B 5/4035* (2013.01); *A61B 5/4058* (2013.01); *G06Q 10/107* (2013.01)

(56) References Cited

U.S. PATENT DOCUMENTS

| | | | | |
|---|---|---|---|---|
| 9,511,289 | B2* | 12/2016 | Bond | A63F 13/212 |
| 2009/0131764 | A1* | 5/2009 | Lee | A61B 5/0205 |
| | | | | 600/301 |
| 2009/0253996 | A1* | 10/2009 | Lee | A61B 5/0476 |
| | | | | 600/544 |
| 2011/0105857 | A1 | 5/2011 | Zhang et al. | |
| 2011/0300847 | A1* | 12/2011 | Quy | H04W 4/00 |
| | | | | 455/419 |

OTHER PUBLICATIONS

Harmon-Jones, E., & Allen, J. J. (1998). Anger and frontal brain activity: EEG asymmetry consistent with approach motivation despite negative affective valence. Journal of Personality and Social Psychology, 74(5), 1310-1316. doi:10.1037//0022-3514.74.5.1310.*

Herrero, N., Gadea, M., Rodríguez-Alarcón, G., Espert, R., & Salvador, A. (2010). What happens when we get angry? Hormonal, cardiovascular and asymmetrical brain responses. Hormones and Behavior, 57(3), 276-283. doi:10.1016/j.yhbeh.2009.12.008.*

Carver, C. S., & Harmon-Jones, E. (2009). Anger is an approach-related affect: Evidence and implications.Psychological Bulletin,135(2), 183-204. doi:10.1037/a0013965.*

Frederickson, J. D. (2010). "Im Sorry, Please Dont Hurt Me": Effectiveness of Apologies on Aggression Control.The Journal of Social Psychology,150(6), 579-581. doi:10.1080/00224540903365356.*

Harmon-Jones, E. (2003). Clarifying the emotive functions of asymmetrical frontal cortical activity.Psychophysiology,40(6), 838-848. doi:10.1111/1469-8986.00121.*

De Pascalis, V. (1998). EEG activity and heart rate during recall of emotional events in hypnosis: relationships with hypnotizability and suggestibility.International Journal of Psychophysiology,29(3), 255-275. doi:10.1016/s0167-8760(98)00009-9.*

Spiridon, E., & Fairclough, S. H. (2009). Detection of anger with and without control for affective computing systems.2009 3rd International Conference on Affective Computing and Intelligent Interaction and Workshops. doi:10.1109/acii.2009.5349586.*

Kubo K et al., entitled "Apology suppresses physiological but not psychological anger," Japanese Cognitive Science Society, Sep. 23, 2011, pp. 32-35, with English Abstract.

Kubo K et al., entitled "Anger is suppressed by single-word apology—Investigation by central/autonomic/subjective index—Apology suppresses physiological but not psychological anger," Japanese Cognitive Science Society, Sep. 23, 2011, pp. 32-35, with English Abstract.

PCT International Search Report, dated Apr. 23, 2013 in connection with PCT International Application No. PCT/JP2013/057623, with English translation, 4 pages.

Kubo K et al., entitled "Apology Isn't Good Enough: An Apology Suppresses an Approach Motivation but Not the Physiological and Psychological Anger," 2012, http://www.plosone.org/article/info:doi/10.1371/journal.pone.0033006.

* cited by examiner

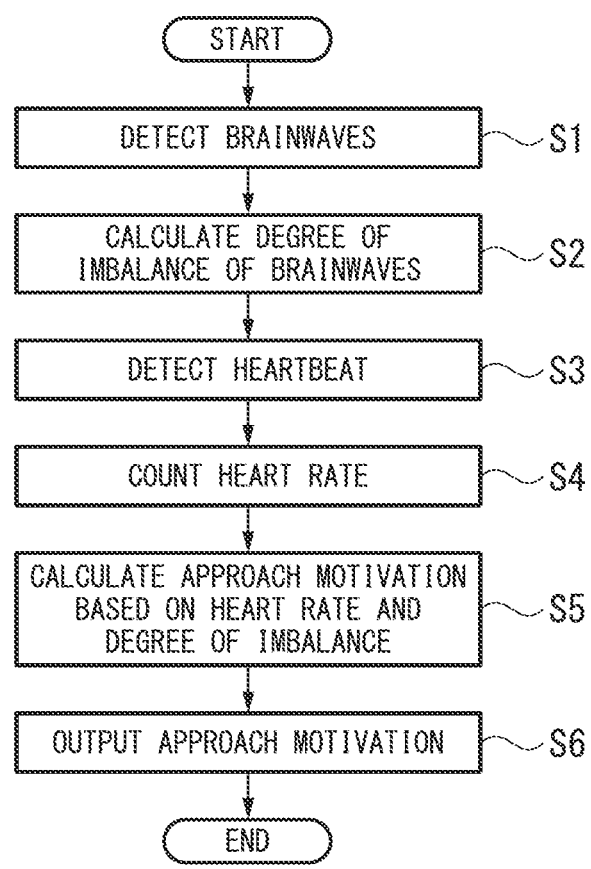

EMOTION IDENTIFICATION DEVICE, EMOTION IDENTIFICATION METHOD, AND EMOTION IDENTIFICATION PROGRAM

CROSS-REFERENCE TO RELATED APPLICATIONS

This application is a U.S. national phase of PCT Application No. PCT/JP2013/057623, filed Mar. 18, 2013, which claims priority to Japanese Application No. JP 2012-174946, filed Aug. 7, 2012, the contents of which are incorporated by reference herein.

TECHNICAL FIELD

The present invention relates to an emotion identification device, an emotion identification method, and an emotion identification program for identifying an emotion.

Introduction

In modern society, the control of anger is very important. This is because sudden anger may cause severe incidents. Anger can be divided into aggressiveness and discomfort. Aggressiveness is an urge to attack or interfere with another party, among a type of approach motivation (see Non-Patent Document 1;

Kenta Kubo and two other persons, "Anger is suppressed by single-word apology—Investigation by central/autonomic/subjective index—Apology suppresses physiological but not psychological anger." Japanese Cognitive Science Society, Sep. 23, 2011, pp. 32 to 35).

SUMMARY OF THE INVENTION

Problem to be Solved by the Invention

However, conventionally, there is a problem in that, when identifying anger in a user, it is difficult to identify aggressiveness in anger by distinguishing it from discomfort in anger. Without identifying aggressiveness in anger by distinguishing it from discomfort in anger, it may be difficult for users to control their anger.

The present invention has been made in view of the above-described circumstances. An object of the present invention is to provide an emotion identification device, an emotion identification method, and an emotion identification program capable of identifying aggressiveness in anger by distinguishing itr from discomfort in anger.

Means for Solving the Problem

The present invention has been made to solve the above-described problem.
An emotion identification device according to an aspect of the present invention includes: a first detection unit which detects a central nervous system reaction of a user; a second detection unit which detects an autonomic nervous system reaction of the user; and an identification unit which identifies aggressiveness in anger of the user based on the central nervous system reaction and the autonomic nervous system reaction.

In the emotion identification device according to the aspect of the present invention, the first detection unit may detect a brainwave as the central nervous system reaction, and the second detection unit may detect a heartbeat as the autonomic nervous system reaction.

In the emotion identification device according to the aspect of the present invention, the first detection unit may detect a brainwave of a left brain of the user and a brainwave of a right brain of the user as the brainwave, and the identification unit may identify the aggressiveness based on a degree of imbalance between the brainwave of the left brain and the brainwave of the right brain and a rate of the heartbeat.

The emotion identification device according to the aspect of the present invention may further include: a calculation unit which calculates the degree of imbalance based on an $\alpha$ power value of the left brain and an $\alpha$ power value of the right brain.

In the emotion identification device according to the aspect of the present invention, the calculation unit may calculate a ratio between the $\alpha$ power value of the left brain and the $\alpha$ power value of the right brain as the degree of imbalance.

An emotion identification method according to an aspect of the present invention is an emotion identification method in an emotion identification device identifying an emotion, and includes: detecting a central nervous system reaction of a user; detecting an autonomic nervous system reaction of the user; and identifying aggressiveness in anger of the user based on the central nervous system reaction and the autonomic nervous system reaction.

An emotion identification program according to an aspect of the present invention causes a computer to execute: acquiring a central nervous system reaction of a user; acquiring an autonomic nervous system reaction of the user; and identifying aggressiveness in anger of the user based on the central nervous system reaction and the autonomic nervous system reaction.

Effect of the Invention

According to the present invention, the identification unit identifies the aggressiveness in the user's anger based on the central nervous system reaction and the autonomic nervous system reaction. Thereby, it is possible to identify aggressiveness in anger by distinguishing it from discomfort in anger.

BRIEF DESCRIPTION OF THE DRAWINGS

FIG. 3 is a flowchart showing an example of an operation procedure of the emotion identification device in the embodiment of the present invention.

EMBODIMENTS FOR CARRYING OUT THE INVENTION

An embodiment of the present invention will be described in detail with reference to the drawings. An emotion identification device identifies aggressiveness in anger by distinguishing it from discomfort in anger when anger in a user is identified.

First, a configuration example of an emotion identification device will be described.

Figure 1:
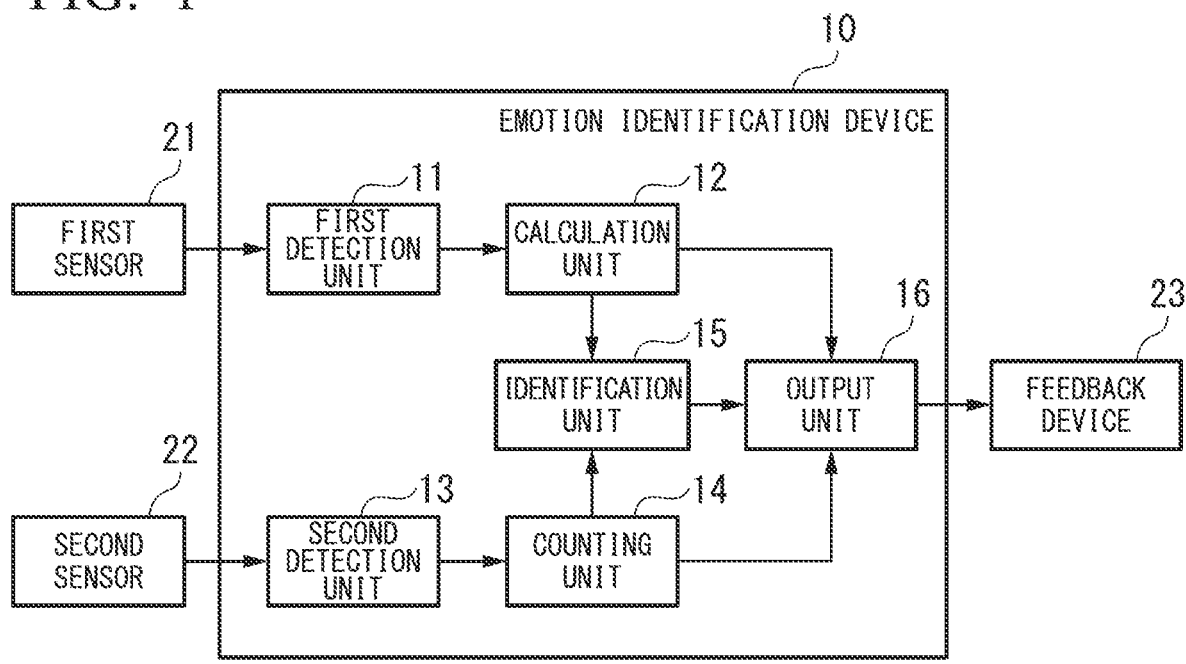
FIG. 1 is a block diagram showing a configuration example of an emotion identification device in an embodiment of the present invention.

In FIG. 1, the configuration example of an emotion identification device is shown by a block diagram. An emotion identification device 10 includes a first detection unit 11, a calculation unit 12, a second detection unit 13, a counting unit 14, an identification unit 15, and an output unit 16.

The first detection unit 11 acquires a sensing result from a first sensor 21 for sensing the central nervous system reaction of the user. The sensor 21 is, for example, provided in a headgear mounted on a head portion of the user. The first detection unit 11 detects brainwaves serving as the central nervous system reaction of the user for a left brain and a right brain.

The first detection unit 11 detects a power value of $\alpha$ waves of the left brain (hereinafter referred to as a "left $\alpha$ power value") by performing a fast Fourier transform (FFT) on the detected brainwaves of the left brain. The first detection unit 11 outputs a signal indicating the detected left $\alpha$ power value to the calculation unit 12. Likewise, the first detection unit 11 detects a power value of $\alpha$ waves of the right brain (hereinafter referred to as a "right $\alpha$ power value") by performing a fast Fourier transform on the detected brainwaves of the right brain. The first detection unit 11 outputs a signal indicating the detected right $\alpha$ power value to the calculation unit 12. Hereinafter, in the description, a state in which the left $\alpha$ power value is less than the right $\alpha$ power value will be assumed to be a state in which the user is angry. The $\alpha$ power value is inversely related to the strength of brain activity. Therefore, the activity of the left brain is predominant in a state in which the left $\alpha$ power value is less than the right $\alpha$ power value.

The calculation unit 12 receives the signal indicating the left $\alpha$ power value and the signal indicating the right $\alpha$ power value from the first detection unit 11. The calculation unit 12 calculates the degree of imbalance e (asymmetry of alpha power) based on the $\alpha$ power value of the left brain and the $\alpha$ power value of the right brain. The calculation unit 12 outputs a signal indicating the calculated degree of imbalance e to the identification unit 15 and the output unit 16. The calculation unit 12 calculates a ratio between the left $\alpha$ power value and the right $\alpha$ power value as the degree of imbalance e.

The calculation unit 12 may calculate a difference value between the left $\alpha$ power value and the right $\alpha$ power value as the degree of imbalance e. The calculation unit 12 may multiply the left $\alpha$ power value and the right $\alpha$ power value by respective weighting factors. The calculation unit 12 may output the signal indicating the left $\alpha$ power value and the signal indicating the right $\alpha$ power value as well as the signal indicating the degree of imbalance e to the output unit 16.

The second detection unit 13 acquires a sensing result from a second sensor 22 for sensing the autonomic nervous system reaction of the user. The sensor 22 is, for example, provided in a band mounted on a wrist or the like of the user. The second detection unit 13 detects a heartbeat serving as the autonomic nervous system reaction of the user and outputs a signal indicating a timing of the heartbeat to the counting unit 14. The second detection unit 13 may detect at least one of skin temperature and skin conductance (SC) serving as the autonomic nervous system reaction and output a signal indicating this detection result to the counting unit 14. Hereinafter, in the description, the heartbeat, the skin temperature, and the skin conductance will be assumed to increase when the user is in a state of anger.

The counting unit 14 receives a signal indicating the timing of the heartbeat from the second detection unit 13. The counting unit 14 counts the heart rate (HR) b per minute (beats per minute: bpm) based on the heartbeat timing. The counting unit 14 outputs a signal indicating the counted heart rate b per minute to the identification unit 15 and the output unit 16.

The identification unit 15 receives the signal indicating the degree of imbalance e from the calculation unit 12. In addition, the identification unit 15 receives the signal indicating the heart rate b per minute from the counting unit 14. The identification unit 15 identifies aggressiveness in the user's anger based on the central nervous system reaction and the autonomic nervous system reaction. That is, the identification unit 15 identifies the aggressiveness in the user's anger based on the degree of imbalance e according to the central nervous system reaction and the heart rate according to the autonomic nervous system reaction. The identification unit 15 calculates approach motivation (AM) as the strength of aggressiveness (a gauge of anger) in the user's anger. The identification unit 15 outputs a signal indicating the calculated approach motivation to the output unit 16.

Figure 2:
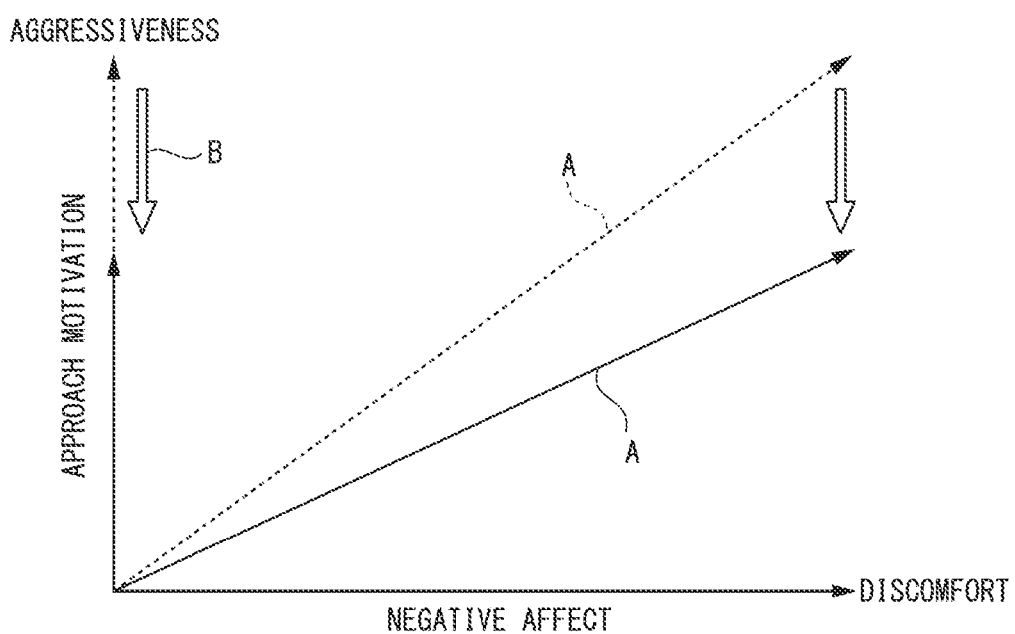
FIG. 2 is a diagram for explaining aggressiveness and discomfort in anger in the embodiment of the present invention.

FIG. 2 is a diagram for explaining aggressiveness and discomfort in anger. The vertical axis of FIG. 2 represents the approach motivation (AM). The approach motivation (−a) is strength based on the degree of imbalance e and the heart rate b (HR). An example of the approach motivation is expressed by Formula (1).

$$-a=\sqrt{(e^2+b^2)} \qquad \text{Formula (1)}$$

Here, "e" denotes the degree of imbalance. "b" denotes the heart rate per minute. For example, when the degree of imbalance e is a value obtained by dividing the left $\alpha$ power value by the right $\alpha$ power value, the degree of imbalance e is a value of 100 or less as a standard. This value is a value close to a human heart rate per minute.

The horizontal axis of FIG. 2 represents the negative affect (NA). The negative affect is strength based on at least one of the skin temperature and the skin conductance (SC), and is strength indicating whether the user feels pleasant or uncomfortable.

In FIG. 2, anger A is conceptually indicated by a vector. As shown in FIG. 2, components of anger A can be classified into aggressiveness and discomfort. The fact that an apology B can suppress aggressiveness in anger, but cannot suppress discomfort is conceptually indicated by the vector.

Returning to FIG. 1, the description of the configuration example of the emotion identification device will continue. The output unit 16 receives the signal indicating the degree of imbalance e from the calculation unit 12. In addition, the output unit 16 receives the signal indicating the heart rate b per minute from the counting unit 14. In addition, the output unit 16 receives the signal indicating the approach motivation from the identification unit 15.

The output unit 16 outputs the signal indicating the degree of imbalance e as a signal for monitoring the brainwaves to a feedback device 23. The output unit 16 may output the signal indicating the left $\alpha$ power value and the signal indicating the right $\alpha$ power value as signals for monitoring the brainwaves to the feedback device 23.

The output unit 16 outputs the signal indicating the heart rate b per minute as a signal for monitoring the heartbeat to the feedback device 23. The output unit 16 outputs the signal indicating the approach motivation to the feedback device 23. Thereby, the degree of imbalance e, the heart rate b per minute, and the approach motivation (−a) are fed back to the user via the feedback device 23. The feedback device 23 may be, for example, a display device or an audio output device for displaying or audibly outputting the degree of imbalance e, the heart rate b per minute, and the approach motivation (−a).

As described above, the emotion identification device 10 can identify aggressiveness (approach motivation) in anger by distinguishing it from discomfort (negative affect) of the anger (see FIG. 2). Thus, the user can easily control his/her anger based on the approach motivation fed back from the emotion identification device 10.

Next, an example of an operation procedure of the emotion identification device will be described.

FIG. 3 is a flowchart showing an example of an operation procedure of the emotion identification device.

(Step S1) The first detection unit 11 detects brainwaves serving as the central nervous system reaction of the user for each of a left brain and a right brain. The first detection unit 11 outputs a signal indicating a left α power value and a signal indicating a right α power value to the calculation unit 12.

(Step S2) The calculation unit 12 calculates a degree of imbalance e based on the α power value of the left brain and the α power value of the right brain. The calculation unit 12 outputs a signal indicating the calculated degree of imbalance e to the identification unit 15 and the output unit 16.

(Step S3) The second detection unit 13 detects a heartbeat serving as the autonomic nervous system reaction of the user and outputs a signal indicating a heartbeat timing to the counting unit 14.

(Step S4) The counting unit 14 counts a heart rate b per minute based on the heartbeat timing. The counting unit 14 outputs a signal indicating the counted heart rate b per minute to the identification unit 15 and the output unit 16.

(Step S5) The identification unit 15 identifies aggressiveness in the user's anger based on the degree of imbalance e according to the central nervous system reaction and the heart rate according to the autonomic nervous system reaction. The identification unit 15 calculates approach motivation as the strength of aggressiveness (for example, a gauge of anger) in the user's anger. The identification unit 15 outputs a signal indicating the calculated approach motivation to the output unit 16.

(Step S6) The output unit 16 outputs the signal indicating the approach motivation to the feedback device 23. Thereby, the approach motivation (−a) is fed back to the user via the feedback device 23.

Next, examples of applications to which the emotion identification device is applied will be described.

<Non-Face-to-Face Communication Application>

The emotion identification device 10 identifies aggressiveness (approach motivation) in anger of a user who desires to write and transmit an e-mail by distinguishing it from discomfort (negative affect) in the anger. In this case, the emotion identification device 10, for example, may be configured as follows.

The emotion identification device 10 identifies the approach motivation of the user writing the e-mail and determines whether a predetermined condition has been satisfied. When the above-described predetermined condition has been satisfied, the emotion identification device 10 provides a notification that the user has written the e-mail in a state in which his/her approach motivation is high (at a predetermined threshold or more) at a predetermined timing. The predetermined timing is, for example, a timing at which the user has selected a transmission button of the e-mail or a timing at which the above-described predetermined condition has been satisfied. At this time, the emotion identification device 10 outputs a message (hereinafter referred to as "confirmation message") for confirming whether to actually transmit the written e-mail. At this time, the e-mail has yet to be transmitted. The emotion identification device 10 transmits the non-transmitted e-mail when the user inputs an indication indicating that the written e-mail may be transmitted, in response to the confirmation message.

When the above-described predetermined condition has been satisfied, the emotion identification device 10 may generate data indicating that the user has not actually apologized (that the approach motivation is high) and transmit the mail with the generated data attached thereto. On the other hand, when the above-described predetermined condition has not been satisfied, the emotion identification device 10 may generate data indicating that the user has actually apologized (the approach motivation is low) and transmit the mail with the generated data attached thereto.

<Medical Application>

In order to rehabilitate a patient having a disorder in communication due to a difficulty inferring the emotions of others, the emotion identification device 10 may identify aggressiveness (approach motivation) in the patient's anger by distinguishing it from discomfort (negative affect) in the anger. This identification result may help to treat the patient.

For example, the emotion identification device 10 provides a notification of whether the approach motivation of the patient is high (at a predetermined threshold or more) at a predetermined timing. The predetermined timing is, for example, a timing at which a counselor has finished talking to the patient. Thereby, the counselor can perform counseling appropriate for the patient based on the notification.

<Environmental Application>

The emotion identification device 10 may identify aggressiveness (approach motivation) in anger of a user who is driving a passenger car by distinguishing it from discomfort (negative affect) in the anger. For example, when the emotion identification device 10 identifies that the approach motivation of the user is greater than or equal to a predetermined threshold value, it may output a self-check message for preventing a driving operation error from an audio output device serving as a feedback device. In addition, when the emotion identification device 10 identifies that the approach motivation of the user is greater than or equal to the predetermined threshold value, it may prevent the driving operation error by restricting the movement of an accelerator of the passenger car.

<Business Application>

The emotion identification device 10 may identify, for example, approach motivation of a user belonging to a management hierarchy in a marketing company and display a message for self-counseling of anger control on a display device serving as the feedback device. A predetermined timing is, for example, a timing at which the user has finished talking to the subordinates. In addition, for example, the emotion identification device 10 may identify the approach motivation of a user belonging to the service industry and display a message for the self-counseling of anger control on the display device serving as the feedback device at a predetermined timing. The predetermined timing is, for example, a predetermined interval when dealing with customers.

As described above, the emotion identification device 10 includes the first detection unit 11 which detects a central nervous system reaction of a user, the second detection unit 13 which detects an autonomic nervous system reaction of the user, and the identification unit 15 which identifies aggressiveness in anger of the user based on the central nervous system reaction and the autonomic nervous system reaction.

With this configuration, the identification unit 15 identifies the aggressiveness in the user's anger based on the central nervous system reaction and the autonomic nervous system reaction with the second detection unit 13 detecting the user's autonomic nervous system reaction. Thereby, the emotion identification device can identify the aggressiveness by distinguishing it from discomfort in anger. In addition, the emotion identification device 10 can identify aggressiveness in anger by distinguishing it from discomfort in anger without confused by the user's voice or expression.

The first detection unit 11 may detect a brainwave as the central nervous system reaction, and the second detection unit 13 may detect a heartbeat as the autonomic nervous system reaction.

The first detection unit 11 may detect a brainwave of a left brain of the user and a brainwave of a right brain of the user as the brainwave. The identification unit 15 may identify the aggressiveness based on a degree of imbalance (for example, left superiority) between the brainwave of the left brain and the brainwave of the right brain and a rate of the heartbeat.

The emotion identification device may further include the calculation unit 12 which calculates the degree of imbalance based on an α power value of the left brain and an α power value of the right brain.

The calculation unit 12 may calculate a ratio between the α power value of the left brain and the α power value of the right brain as the degree of imbalance.

An emotion identification method is an emotion identification method in an emotion identification device identifying an emotion, and includes: detecting a central nervous system reaction of a user; detecting an autonomic nervous system reaction of the user; and identifying aggressiveness in anger of the user based on the central nervous system reaction and the autonomic nervous system reaction.

An emotion identification program causes a computer to execute: acquiring a central nervous system reaction of a user; acquiring an autonomic nervous system reaction of the user; and identifying aggressiveness in anger of the user based on the central nervous system reaction and the autonomic nervous system reaction.

While the embodiment of the present invention has been described and illustrated in detail above with reference to the drawings, specific configurations are not limited to the embodiment, and a design change and the like are also be included without departing from the scope of the present invention.

Processing may be performed by recording a program for implementing the above-described emotion identification device on a computer-readable recording medium and causing a computer system to read and execute the program recorded on the recording medium. The "computer system" used here may include an OS, and hardware such as peripheral devices.

The "computer system" also includes a homepage providing environment (or displaying environment) when a WWW system is used. The "computer-readable recording medium" refers to a storage apparatus, including a flexible disk, a magneto-optical disc, a ROM, a writable non-volatile memory such as a flash memory, a portable medium such as a CD-ROM, and a hard disk embedded in the computer system.

The "computer-readable recording medium" also includes a medium that holds a program for a constant period of time, such as a volatile memory (e.g., a dynamic random access memory (DRAM)) inside a computer system serving as a server or a client when the program is transmitted via a network such as the Internet or a communication circuit such as a telephone circuit.

The above-described program may be transmitted from a computer system storing the program in a storage apparatus or the like via a transmission medium or transmitted to another computer system by transmission waves in a transmission medium. The "transmission medium" for transmitting the program refers to a medium having a function of transmitting information, such as a network (communication network) like the Internet or a communication circuit (communication line) like a telephone circuit.

The above-described program may implement some of the above-described functions.

The above-described program may be one capable of implementing the above-described function in combination with a program already recorded on the computer system, is which a so-called differential file (differential program).

INDUSTRIAL APPLICABILITY

The present invention can be applied to an emotion identification device, an emotion identification method, and an emotion identification program for identifying an emotion. According to the emotion identification device, the emotion identification method, and the emotion identification program to which the present invention has been applied, it is possible to identify aggressiveness in anger by distinguishing it from discomfort in anger.

REFERENCE SYMBOLS

10 Emotion identification device
11 First detection unit
12 Calculation unit
13 Second detection unit
14 Counting unit
15 Identification unit
16 Output unit

The invention claimed is:

1. A computer system for identifying a level of aggressiveness in anger of a user writing an email and for displaying or audibly outputting to the user the level of aggressiveness as approach motivation, the computer system comprising:
   a headgear brainwave sensor which is provided in a headgear mounted on a head portion of the user, the headgear brainwave sensor detecting a brainwave signal of a left brain of the user and a brainwave signal of a right brain of the user;
   a first detection unit which is coupled to the headgear brainwave sensor, the first detection unit acquiring a sensing result from the headgear brainwave sensor, the first detection unit performing a fast Fourier transformation on the detected brainwave signal of the left brain so as to obtain an α power value of the left brain, the first detection unit performing a fast Fourier transformation on the detected brainwave signal of the right brain so as to obtain an α power value of the right brain;
   a calculation unit which calculates a degree of imbalance, the degree of imbalance being a value obtained by dividing the α power value of the left brain by the α power value of the right brain;
   a wrist mounted heartbeat sensor which is provided in a band mounted on a wrist of the user, the wrist mounted heartbeat sensor detecting a heartbeat of the user;

a second detection unit which is coupled to the wrist mounted heartbeat sensor, the second detection unit acquiring a sensing result from the wrist mounted heartbeat sensor;

a counting unit which counts a heart rate per minute based on a timing of the detected heartbeat;

an identification unit which calculates a square root of a sum of square of the degree of imbalance and square of the heart rate per minute to acquire approach motivation so as to identify the level of aggressiveness in anger of the user;

an output unit which outputs the calculated approach motivation and the heart rate per minute; and a display or audio feedback device which displays or audibly outputs the output approach motivation and the heart rate per minute, wherein the computer system is configured to provide a notification to the user, who has written an email, via the display or audio feedback device of the computer system prior to transmission of the email confirming the identified level of aggressiveness in anger of the user as being at or above a predetermined threshold level and when the level of aggressiveness in anger of the user is identified as at or above the predetermined threshold level, (i) configured to transmit data for transmission with the email indicating the identified level of aggressiveness in anger of the user, or (ii) configured not to transmit the email when the calculated approach motivation of the user is at or above a predetermined threshold and (a) to provide, at a predetermined timing, a notification to the user who has written the email that his/her approach motivation is at a predetermined threshold or more and (b) require from the user an input of confirmation of transmission, and (c) not subsequently transmit the email unless the user has inputted a confirmation of transmission of the email.

2. A method performed by a computer system for identifying a level of aggressiveness in anger of a user and displaying or audibly outputting to the user the level of aggressiveness as approach motivation, the method comprising:

detecting, by a headgear brainwave sensor of the computer system, a brainwave signal of a left brain of the user and a brainwave signal of a right brain of the user, the headgear brainwave sensor being provided in a headgear mounted on a head portion of the user;

performing, by the computer system, a fast Fourier transformation on the brainwave signal of the left brain so as to obtain an α power value of the left brain;

performing, by the computer system, a fast Fourier transformation on the brainwave signal of the right brain so as to obtain an α power value of the right brain;

calculating, by the computer system, a degree of imbalance, the degree of imbalance being a value obtained by dividing the α power value of the left brain by the α power value of the right brain;

detecting, by a wrist mounted heartbeat sensor of the computer system, a heartbeat of the user, the wrist mounted heartbeat sensor being provided in a band mounted on a wrist of the user;

counting, by the computer system, a heart rate per minute based on a timing of the detected heartbeat;

calculating, by the computer system, a square root of a sum of square of the degree of imbalance and square of the heart rate per minute to acquire approach motivation so as to identify the level of aggressiveness in anger of the user;

outputting, by the computer system, the calculated approach motivation and the heart rate per minute;

displaying or audibly outputting the output approach motivation and the heart rate per minute;

providing, by the computer system, a notification to the user, who has written an email, via a display or audio feedback device of the computer system prior to transmission of the email confirming the identified level of aggressiveness in anger of the user as being at or above a predetermined threshold level; and when the level of aggressiveness in anger of the user is identified as at or above the predetermined threshold level, (i) transmitting the email with data indicating the identified level of aggressiveness in anger of the user, or (ii) not transmitting the email when the calculated approach motivation of the user is at or above a predetermined threshold and (a) providing, at a predetermined timing, a notification to the user who has written the email that his/her approach motivation is at a predetermined threshold or more and (b) requiring an input of confirmation of transmission, and (c) not subsequently transmitting the email unless the user has inputted the confirmation of transmission of the email.

3. A non-transitory computer-readable recording medium storing a program for identifying a level of aggressiveness in anger of a user and for displaying or audibly outputting to the user the level of aggressiveness as approach motivation, wherein the program causes;

a headgear brainwave sensor of a computer system to detect a brainwave signal of a left brain of the user and a brainwave signal of a right brain of the user, the headgear brainwave sensor being provided in a headgear configured for a head portion of the user, and the computer system to execute:

performing a fast Fourier transformation on the brainwave signal of the left brain so as to obtain an α power value of the left brain;

performing a fast Fourier transformation on the brainwave signal of the right brain so as to obtain an α power value of the right brain; and calculating a degree of imbalance, the degree of imbalance being a value obtained by dividing the α power value of the left brain by the α power value of the right brain, a wrist mounted heartbeat sensor of the computer system to detect a heartbeat of the user, the wrist mounted heartbeat sensor being provided in a band mounted on a wrist of the user, and the computer system to execute:

counting a heart rate per minute based on a timing of the detected heartbeat;

calculating a square root of a sum of square of the degree of imbalance and square of the heart rate per minute to acquire approach motivation so as to identify a level of aggressiveness in anger of the user;

outputting the calculated approach motivation and the heart rate per minute;

displaying or audibly outputting the output approach motivation and the heart rate per minute;

providing a notification to the user, who has written an email, via a display or audio feedback device of the computer system prior to transmission of the email confirming the identified level of aggressiveness in anger in of the user as being at or above a predetermined threshold level; and when the level of aggressiveness in anger of the user is identified as at or above the predetermined threshold level, (i) transmitting the email with data indicating the identified level of aggressiveness in anger of the user, or (ii) not transmitting the email when the calculated approach motivation of the user is at or above a predetermined threshold and (a) providing, at a predetermined timing, a notification to the user who has written the email that his/her approach motivation is at a predetermined threshold or more and (b) requiring an input of confirmation of transmission, and (c) not subsequently transmitting the email unless the user has inputted the confirmation of transmission of the email.

* * * * *